US008870980B2

(12) United States Patent
Malm et al.

(10) Patent No.: US 8,870,980 B2
(45) Date of Patent: Oct. 28, 2014

(54) PROCESS FOR PRODUCING ENZYMES

(75) Inventors: Annika Malm, Helsinki (FI); Simo Laakso, Turku (FI); Ossi Pastinen, Kantvik (FI); Heidi Kahelin, Espoo (FI); Miia Mujunen, Helsinki (FI)

(73) Assignee: Neste Oil Oyj, Espoo (FI)

( * ) Notice: Subject to any disclaimer, the term of this patent is extended or adjusted under 35 U.S.C. 154(b) by 426 days.

(21) Appl. No.: 13/333,188

(22) Filed: Dec. 21, 2011

(65) Prior Publication Data

US 2012/0159838 A1 Jun. 28, 2012

Related U.S. Application Data

(60) Provisional application No. 61/459,965, filed on Dec. 22, 2010.

(30) Foreign Application Priority Data

Dec. 22, 2010 (EP) ..................................... 10196423

(51) Int. Cl.
| | | |
|---|---|---|
| *C10L 1/18* | (2006.01) | |
| *C12N 9/00* | (2006.01) | |
| *C12N 9/24* | (2006.01) | |
| *C12P 7/64* | (2006.01) | |
| *C12N 9/42* | (2006.01) | |

(52) U.S. Cl.
CPC *C12N 9/00* (2013.01); *C12N 9/248* (2013.01); *Y02E 50/16* (2013.01); *Y02E 50/17* (2013.01); *C12P 7/6463* (2013.01); *Y02E 50/13* (2013.01); *C12N 9/2437* (2013.01)
USPC .................. 44/307; 44/385; 44/388; 435/183; 435/189; 435/193; 435/195; 435/232; 435/233; 554/174

(58) Field of Classification Search
CPC .......... C10L 1/02; C10L 1/14; C10L 1/1802; C12N 9/14; C12N 9/88; C12N 9/93; C12P 19/24
USPC ............ 44/307, 385; 435/183, 189, 193, 195, 435/232, 233; 554/174
See application file for complete search history.

(56) References Cited

U.S. PATENT DOCUMENTS

| 7,691,792 B1 | 4/2010 | Fisher et al. |
| 2009/0064567 A1 | 3/2009 | Lippmeier et al. |
| 2009/0217569 A1* | 9/2009 | Pastinen et al. .................. 44/308 |

FOREIGN PATENT DOCUMENTS

| EP | 1396531 | 3/2004 |
| EP | 1398364 | 3/2004 |
| EP | 1741767 | 1/2007 |
| EP | 1741768 | 1/2007 |
| WO | 2006031937 | 3/2006 |
| WO | 2008151149 | 12/2008 |
| WO | 2010129101 | 11/2010 |
| WO | 2010149859 | 12/2010 |
| WO | 2011103428 | 8/2011 |

OTHER PUBLICATIONS

Aachary et al., "Corncob-induced endo-1,4-beta-D-Xylanase of *Aspergillus oryzae* MTCC 5154: Production and characterization of xylobiose from glucuronoxylan", J. Agric. Food Chem., 2008, 56:3981-3988.
Chipeta et al., "Effect of cultivation pH and agitation rate on growth and xylanase production by *Aspergillus oryzae* in spent sulphite liquor", J Ind Microbiol Biotechnol, 2008, 35:587-594.
Hsiao et al., "Broth Recycle in a Yeast Fermentation", Biotechnology and Bioengineering, 1994, 44:1228-1234.
Hui et al., "Direct microbial conversion of wheat straw into lipid by a cellulolytic fungus of *Aspergillus oryzae* A-4 in solid-state fermentation", Bioresource Technology, 2010, 101:7556-7562.
Ismail et al., "Production of Hemicellulytic Enzymes by Fungi", Agricultural Wastes, 1986, 18:283-288.
Kocabas et al., "Optimization of xylanase production from *Aspergillus terreus* by using renewable agricultural lignocellulosic residues", New Biotechnology, Sep. 2009, 255:S145.
Peng et al., "Microbial oil accumulation and cellulase secretion of the endophytic fungi from oleaginous plants", Annals of Microbiology, 2007, 57(2):239-242.
Suutari et al., "Temperature adaptation in yeasts: the role of fatty acids", Journal of General Microbiology, 1990, 136:1469-1474.
Szczesna-Antczak et al., "Relationsihps between lipases and lipids in mycelia of two Mucor strains", Enzyme and Microbial Technology, 2006, 29:1214-1222.
Abstract for WO2006093347, Sep. 2006.
European Search Report for EP10196423 dated May 11, 2011.
International Search Report and Written Opinion for PCT/FI2011/051134 dated Apr. 23, 2012.

* cited by examiner

*Primary Examiner* — Cephia D Toomer
(74) *Attorney, Agent, or Firm* — Andrus Intellectual Property Law, LLP

(57) ABSTRACT

The present invention relates to a process for producing enzymes and single cell oil. The process comprises that microorganisms capable of producing both single cell oil and enzymes are cultivated under conditions suitable for single cell oil production and enzyme production in a single cell oil production process. A microorganism culture comprising single cell oil and enzymes is obtained and at least part of the microorganism culture, of the supernatant and/or microorganism cells separated from the microorganism culture, of protein fraction enriched from the supernatant, and/or of protein fraction obtained from the cells is used as an enzyme preparation or as a source of enzymes. Single cell oil is recovered from the microorganism cells and used as biofuel, component of biofuel or as a starting material for biofuel production. Enzymes produced according to the process are used in the same or in another industrial process.

14 Claims, 8 Drawing Sheets

PROCESS FOR PRODUCING ENZYMES

CROSS-REFERENCE TO RELATED APPLICATIONS

The present application claims the benefit of priority under 35 U.S.C. §119(e) to U.S. Provisional Application No. 61/459,965, filed on Dec. 22, 2010, the content of which is incorporated herein by reference in its entirety.

FIELD

The present invention relates to a process for producing enzymes. In particular, the present invention relates to a process for producing enzymes in a single cell oil process and the utilization of the enzymes in the same or other processes.

BACKGROUND

Certain microorganisms are capable of accumulating intracellular triacylglycerol, single-cell oil, under suitable physiological conditions. This property has been utilized for production of single-cell oils mainly for specialty use and high value products, such as cosmetics and nutritional applications. Up to date the need of single-cell oils for these purposes has been satisfied by low or moderate scale production processes in which process economy and sustainability of production have not played a significant role.

At present there is increasing interest for the use of non-fossil raw materials as alternatives for the fossil ones as precursors of transportation fuel. The main challenge appears to be that the production of single-cell oil should be carried out in such a large scale that problems typical for large scale aqueous microbial processes are evitable. Characteristically a single-cell oil production process requires high energy input and produces large aqueous side streams and single cell debris. Thus, the current technology for ultra large-scale aqueous microbial processes does not seem economically feasible and includes several problems with respect to environmental issues.

Carbohydrates are the richest single reserve of biomass on the earth and thus the only realistic substrate for large scale single-cell oil production. Lignocelluloses are the most abundant source of carbohydrates on Earth. However, lignocellulosic or other composite biomaterials require extensive processing to make them available for microorganisms as nutrients and as the source of single cell oil. Concomitantly with the processing of lignocellulosic biomass, non-fermentable side streams, such as lignin, will arise. On the other hand, the single cell oil production process itself yields cell mass and side streams, which still contain a fair amount of nutrients.

The re-utilization of the side streams of various fermentation processes and improvement of the overall process economy has been suggested in some publications in the prior art. The quantitatively dominating side streams of single-cell oil production are fermentation waste water and cell debris remaining after removal of oil from the cells. US 2009/0064567 A1 discloses the production of biological oils by heterotrophic fermentation by growing microorganism of the kingdom Stramenopile. The publication suggests the re-cycling of de-lipidated biomass or hydrolyzed biomass to media used for cultivation of the microorganism.

SUMMARY

It is one object of the present invention to provide a solution to problems encountered in the prior art. Specifically, the present invention aims to provide a technically beneficial solution to problems encountered in the large-scale production of single-cell oil.

In particular, it is one object of the present invention to provide a solution, which enables upgrading the economy of large-scale single-cell oil production.

It is another object of the present invention to provide a solution, which enables reducing the environmental burden caused by large-scale single-cell oil production.

The present invention aims particularly to work out problems related to the manufacture of transportation biofuel.

To achieve these objects the invention is characterized by the features that are enlisted in the independent claims. Other claims represent the preferred embodiments of the invention.

The method according to the invention is based on the finding that the side streams of single cell oil production process comprise a significant amount of nutrients, which can serve as carbon source for microorganisms, for example for oil producing microorganisms.

It has now been surprisingly found that the side streams of single cell oil production process comprise also a significant amount of proteins, in particular enzymes. Hence, the microorganism culture or its fractions can be used as a source of enzymes or as enzyme preparations or as components of enzyme preparations.

In one aspect, the present invention provides a process for producing enzymes, which comprises that a microorganism capable of producing both single cell oil (lipids) and enzymes is cultivated under conditions suitable for lipid production and suitable for enzyme production, and single cell oil (lipids) and enzymes are produced by said microorganism.

In one embodiment of the invention the microorganism culture comprising microorganism cells and spent culture medium is recovered.

In another embodiment of the invention the supernatant and/or microorganism cells are separated from the microorganism culture and the supernatant and/or the cells are recovered.

Yet, in another embodiment of the invention the protein fraction is enriched in the microorganism culture or in the supernatant and the enriched protein fraction is recovered. This can be achieved for example by concentrating the aqueous phase (culture broth) of microorganism culture or the supernatant.

Yet, in another embodiment of the invention intracellular enzymes produced by the microorganisms are recovered from the cells by autolysis or induced lysis of the cells. Enzymes liberated from the cells can be harvested from the supernatant.

According to a preferred embodiment of the invention the enzymes are recovered from the supernatant. Enzymes excreted to the cultivation medium or released by cell lysis are extracellular and can be recovered from the supernatant.

According to one further embodiment of the invention, the cultivation medium is solid or semisolid and the enzymes are introduced into aqueous phase from which they are recovered.

In various embodiments of the invention the enzymes are recovered from the microorganism culture or its fractions in catalytically active form.

In one embodiment of the invention the microorganism culture or the liquid phase comprising catalytically active enzymes is introduced into the same biotechnical process or the feedstock, such as polymeric biomass, used in said process is pre-treated with said enzymes.

In another embodiment of the invention the microorganism culture or the liquid phase comprising catalytically active enzymes is introduced into another process or the feedstock, such as polymeric biomass, used in said process is pre-treated.

In one further embodiment of the invention the microorganism culture or the liquid phase comprising enzymes produced by the microorganism is introduced into a biotechnical process, which uses a microorganism not capable of producing enzymes or the feedstock, such as polymeric biomass, used in said process is pre-treated.

The same or another process is preferably a single cell oil production process.

According to one embodiment of the invention the process is a process using polymeric biomass and/or polymeric sugars, such as lignocellulose as feedstock.

In another embodiment a protein-enriched fraction of the microorganism culture or supernatant is introduced into another industrial process or it is used to treat feedstock fed to another industrial process.

In another embodiment a protein-enriched fraction of the microorganism culture or supernatant is introduced into another biotechnical process or it is used to treat the feedstock, such as polymeric biomass and/or polymeric sugars fed to the other biotechnical process.

In a further embodiment of the invention the protein fraction in the microorganism culture or in the supernatant is enriched, recovered and optionally purified, stabilized, dried and/or formulated and used as an enzyme preparation or as a source of enzymes in various applications.

In a further embodiment of the invention the enzymes are intracellular and obtained from the cells. Intracellular enzymes are recovered and optionally enriched, purified, isolated, stabilized, dried and/or formulated.

The major advantage of the production of single cell oil and enzymes is that the cost efficiency of single cell oil production and environmental facts associated to process side streams are taken into account in the context of large scale single cell oil production. Furthermore, the integrated process results in a more efficient utilization of polymeric biomasses while reducing the biological oxygen demand of the side streams typical for aqueous fermentation processes.

The present invention provides several economical and environmental advantages:

The energy cost of treatment of lignocellulosic materials or materials comprising other polymeric carbohydrate biomass is reduced by using enzymes from the single cell oil process itself in place of commercial enzymes and thermo-mechanical and chemical treatments.

The removal of enzyme proteins from the remainder of the liquors from the single cell oil production fermentation reduces the biological oxygen consumption load of the fermentation liquor released from single cell oil production.

After removal of the cellular material, the essentially cell free fermentation waste liquor is better suited for reuse.

The carbon balance of a single cell oil process is improved when the enzyme proteins, instead of causing biological load in process streams, are reduced or removed from the fermentation waste water, reused for catalytic purposes or used as a nutrient in the single-cell oil production process or other industrial or in particular biotechnical processes.

The enzymes recovered from fermentation liquor can be used for hydrolysis of polymeric compounds of microorganisms or components of microorganisms.

The method according to the invention can be implemented by using known and tested unit operations and industrially applicable microorganism species.

The invention contributes to the economic and technical usability of lignocellulosic material for single cell oil production.

DETAILED DESCRIPTION

Figure 1:
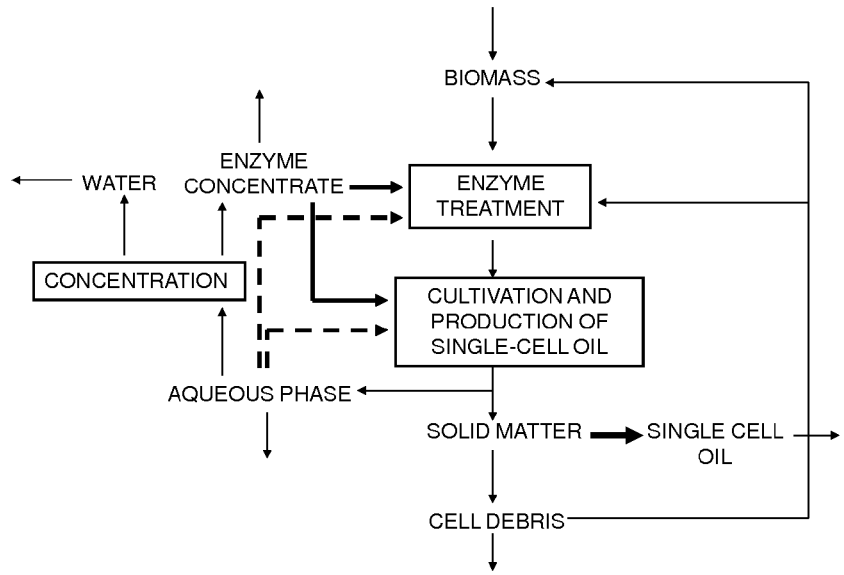
FIG. 1 Process scheme

"A single cell oil production process" refers here to a process, comprising steps of forming or allowing the formation of a lipid synthesizing microorganism and allowing the thus obtained organism mass to produce and/or store (accumulate) lipid, recovering the cells from the liquid phase, and extracting or recovering the lipids from the cells. As described here later in various microorganism groups, such as among bacteria, archaebacteria, fungi (filamentous fungi), yeast and algae, are single cell oil producing microorganisms.

As described herein, the present invention uses preferably microorganisms capable of producing both lipids and enzymes. "A microorganism" refers in some embodiments of the invention to two or more microorganisms. In some embodiments, the enzymes are produced by one microorganism and the single cell oil (lipids) by another microorganism.

The term "single cell oil" refers to a fatty substance, whose molecule generally contains, as a part, an aliphatic hydrocarbon chain, which dissolves in nonpolar organic solvents but is poorly soluble in water. Single cell oils are an essential group of large molecules in living cells. Single cell oils are, for example, lipids, fats, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as triacylglycerols, diacylglycerols, or monoacylglycerols.

Preferred single cell oils in the present invention are lipids, fats, waxes, acylglycerols and fatty acids and their derivatives, in particular triacylglycerols and wax esters.

In connection of this invention "lipid" is used as synonym for single cell oil.

In one aspect the present invention provides a process for producing enzymes, which comprises that a microorganism capable of producing both lipids and enzymes is cultivated under conditions suitable for lipid production and enzyme production in a single cell oil production process. The microorganisms are allowed to produce lipids and enzymes. Single cell oil (lipids) are recovered from the microorganism cells and the microorganism culture and/or culture medium or a part of it or various fractions of the microorganism culture and/or culture medium are used as an enzyme preparation or as a source of enzymes.

In an embodiment of the invention at least part of the microorganism culture comprising microorganism cells and spend culture medium is used as an enzyme preparation or as a source of enzymes.

In an embodiment of the invention the microorganism culture or part thereof or the supernatant or part thereof is re-circulated in the single cell oil process. Typically 10% to 90%, preferably 20% to 80%, in some embodiments 30% to 70%, in some embodiments 40% to 60%, in some embodiments 20% to 50%, of the microorganism culture or of the supernatant is re-circulated in the process, preferably re-circulated back to the single cell oil production process or to the treatment of feedstock.

In another embodiment the supernatant and/or microorganism cells are separated from the microorganism culture and used as an enzyme preparation or as a source of enzymes.

Supernatant stands for a substantially cell-free fraction, which comprises the spent culture medium or culture broth. Supernatant can be called also "fermentation liquid" or "a liquid phase".

The supernatant and cells need not to be separated completely. In some embodiments the supernatant comprises 1% to 50% of the cells of the original microorganism culture. In some embodiments the supernatant comprises 5 to 40%, in some embodiments 5 to 30%, in some embodiments 10 to 40%, or 20 to 30%, or 40 to 50% of the cells of the original microorganism culture.

In some embodiments the cell fraction comprises 1% to 50% of the cells of the original microorganism culture. In some embodiments the cell fraction comprises 5 to 40%, in some embodiments 5 to 30%, in some embodiments 10 to 40%, or 20 to 30%, or 40 to 50% of the cells of the original microorganism culture.

The separation of the supernatant and the cells can be done by any suitable method maintaining the catalytic activity of the enzymes.

A preferred method for recovery of enzymes is a method by which the microorganism culture, the supernatant or any combination thereof can be treated by a person skilled in the art to achieve the recovery of the enzymes while maintaining their catalytic activity.

The enzymes can be recovered from microorganism culture, spent culture medium, supernatant and microorganism cells by any known and suitable method or by any suitable method developed in the future. The same applies also to methods by which the enzymes can be separated into fractions with the desired enzyme activities.

A method by which the microorganism culture or the supernatant or the enriched protein fraction comprising catalytically active enzyme(s) are recovered can be based on their molecular size, ionic behavior, solubility in water, solubility in different solutes or solubility in mixture solutes containing a buffering factor or a surface active factor or a surface-active compound or a salt.

The enzymes can be recovered from the culture medium by various procedures, including but not limited to procedures such as centrifugation, filtration, extraction, spray-drying, evaporation, or precipitation.

If needed the enzymes may be purified or isolated by various procedures including but not limited to chromatograpyhy, electrophoretic procedures, differential solubility, SDS-PAGE, or extraction.

The enzymes may be stabilized for example by salt, sugar or glycerol. Furthermore, the enzymes may be formulated for the desired application. Corresponding methods can be applied when recovering enzymes from the microorganism cells.

In an embodiment the protein fraction is recovered from the microorganism cells. The recovery can be done by any suitable method maintaining the catalytic activity of the enzymes.

"Lipid recovery" refers to a process, in which the lipid (intracellular lipid) is recovered by mechanical, chemical, biochemical, thermomechanical or autocatalytic methods or by a combination of these methods from the microorganism cells.

Single-cell oil stands typically for an intracellular lipid that has been intracellularly synthesized by a microorganism, lipids excreted by the cell, as well as lipids present in the structural parts of a cell, such as in membrane systems. In certain cases, single cell oil can be also extracellular such as excreted or liberated from cells in culture medium during or after cultivation.

"Residual cell mass" stands for a solid, semi-solid or flowing material fraction, which contains microorganisms treated for the recovery of intracellular lipids and/or intracellular enzymes.

"Lipid-containing single cell mass" stands for an autotrophically, heterotrophically and/or mixotrophically formed single-cell mass and cellular mycelium with a lipid content of at least 3%, preferably at least 10%, preferably at least 15% (w/w) or more of dry matter of the microorganism.

The enzyme preparation obtained as described herein is the microorganism culture or the supernatant or the enriched protein fraction comprising catalytically active enzyme. Typically the enzyme preparation is the process water (aqueous phase, culture broth, supernatant) of a single cell oil production process, or the protein fraction enriched from a process water (aqueous phase, culture broth, supernatant). The enrichment can be carried out by any suitable method used for enriching or concentrating proteins in biologically active form.

In an embodiment of the invention the cultivation medium is solid or semisolid and the enzymes are introduced to aqueous phase before recovery.

"Enriching a protein fraction" refers here to any method enriching the proteins from any fraction of the single-cell oil production process and maintaining the catalytic activity of the proteins. More specifically the method comprises that the liquid phase of the microorganism culture or supernatant from a single cell oil production process is treated by at least one method enriching the proteins in the liquid phase. In some embodiment of the invention the enriching process is not necessary.

In some embodiments the protein fraction is enriched at least 10%, typically at least 20%, in various embodiments at least 30%, at least 40%, at least 50%, at least 60%, at least 70%, at least 80%, at least 90%, compared to the original liquid phase. Examples of suitable methods are methods based on ionic properties of proteins, molecule size, solubility, surface active properties or hydrophobic interactions. Preferably the recovery of enzyme fraction is carried out under conditions, where the temperature is 70° C. or lower.

In an embodiment of the invention the protein fraction is enriched in the aqueous phase of the microorganism culture or in the supernatant. The enrichment can be carried out simple for example by concentrating the aqueous phase of the microorganism culture or the supernatant.

In an embodiment of the invention the protein fraction in the aqueous phase of the microorganism culture or in the supernatant is enriched at least 1 time (1×), typically at least 2 times (2×), preferably at least 3 times (3×) calculated as the enzyme activity per volume and/or activity per total protein. In some embodiments the protein fraction in the aqueous phase of the microorganism culture or in the supernatant is enriched at least 5 times, in some embodiments at least 10×, or 20× or 30×, or 40×, or 50×, or 60×, or 70×, or 80×, or 90×, or 100× calculated as the enzyme activity per volume and/or per total protein.

According to a preferred embodiment of the invention the enzymes are recovered from the supernatant. "Extracellular enzymes" are enzymes excreted to the cultivation medium or released by cell lysis from the cells to the cultivation medium. Extracellular enzymes can be recovered from the supernatant.

By "process water" released from the single cell oil process is meant here water released from the process after enzyme recovery. Part of the process water can be circulated back to the process and part of the process water can be circulated or led to another process and part can be released to the environment. The process water can also be led to a waste water treatment process before released to the environment.

In an embodiment of the invention typically 10% to 90%, preferably 20% to 80%, in some embodiments 30% to 70%, in some embodiments 40% to 60%, in some embodiments 20% to 50%, of the process water is re-circulated in the process, preferably re-circulated back to the single cell oil production process or to the treatment of feedstock.

In an embodiment of the invention the process water released from the process contains at least 5%, at least 10%, preferably at least 20%, typically at least 30%, more preferably at least 40%, still more preferably at least 50%, still more preferably at least 60%, still more preferably at least 70%, still more preferably at least 80%, still more preferably at least 90%, less proteins than the process water of a single cell oil process without enzyme recovery.

In an embodiment of the invention the process water released from the process has at least 5%, at least 10%, preferably at least 20%, typically at least 30%, more preferably at least 40%, still more preferably at least 50%, still more preferably at least 60%, still more preferably at least 70% still more preferably at least 80%, still more preferably at least 90% lower biological oxygen demand compared to the biological oxygen demand of a process water of a single cell oil process without enzyme recovery.

In an embodiment of the invention the enzymes are intracellular and obtained from the microorganism cells.

In an embodiment of the invention the cell residues after enzyme recovery contain at least 1%, at least 5%, at least 10%, preferably at least 20% less proteins than the cell residues of a single cell oil process without enzyme recovery from the cells.

In some embodiments the cell residues after enzyme recovery contain at least at least 30%, preferably at least 40%, preferably at least 50%, preferably at least 60%, preferably at least 70% preferably at least 80%, preferably at least 90% less proteins than the cell residues of a single cell oil process without enzyme recovery from the cells.

In an embodiment of the invention the enzyme production and single cell oil production occur simultaneously or sequentially in any order. Typically the enzyme production is started earlier. The produced enzyme degrades the polymeric biomass in the cultivation medium thereby producing components for the growth of the microorganism.

"Enzyme" refers here to any enzyme and is not limited to any specific enzyme or enzyme group. In an embodiment an enzyme refers to an enzyme having an effect to complex carbohydrates and proteins. "Enzyme" refers preferably to hydrolases (EC 3.x.x.), oxidoreductases (EC 1.x.x.), lyases (EC 4.x.x.), isomerases (EC 5.x.x.), transferases (EC 2.x.x.) and ligases (EC 6.x.x.). The first number means enzyme group, first x means type of bond and second x refers to the specific reaction.

By "enzyme" is in the present invention meant in particular an extracellular enzyme capable of degrading complex carbohydrates, proteins and lipids. More specifically the enzyme is a hydrolytic enzyme introducing water to a functional group of the reaction product and thereby degrading a glycosidic, peptide, ester or ether bond or a bond between nitrogen and carbon or nitrogen and oxygen. The enzyme is preferably a cellulase, xylanase, glucosidase, mannanase, galactase, arabinase, pectinase, protease, lipase, phospholipase, isomerase or esterase. A hydrolytic enzyme refers here to an enzyme capable of hydrolysis reaction i.e. capable of transferring functional groups to water. Preferably the enzymes are selected from the group of cellulases, hemicellulases, xylanases, glucosidases, galactosidases or mannanases.

In some embodiments the enzyme is oxidoreductase catalyzing oxidation-reduction reactions, lyase catalyzing addition or removal of groups to form double bonds, isomerase catalyzing intramolecular group transfer or a ligase catalyzing ligation of two substrates at the expense of ATP hydrolysis.

"Cellulase" or "cellulolytic enzyme" refers to a group of enzymes produced mainly by fungi, such as filamentous fungi or yeasts, bacteria, plants of by animals that catalyze the hydrolysis of cellulose, also called as cellulolysis. Several different kinds of cellulases are known, which differ structurally and mechanistically. The general of cellulases include, based on the type of reaction catalyzed, endo-cellulases, exo-cellulases, cellobiases or beta-glucosidases, oxidative cellulases, and cellulose phosphorylases. These enzymes can be found under the following EC numbers such as: EC 3.2.1.4, EC 3.2.1.91, EC 3.2.1.21.

"Hemicellulase" refers to a group of enzymes produced mainly by fungi, such as filamentous fungi or yeasts, bacteria, plants of by animals that catalyze the hydrolysis of hemicellulose. For example, the enzymes involved in the hydrolysis of xylan include endo-xylanases, acetyl-xylanesterases, α-D-glucuronidases, α-L-arabinofuranosidases, ferulic acid esterases and β-Xylosidases. In addition, the enzymes involved in the hydrolysis of galactoglucomannan include endo-mannanases, acetyl-mannanesterases, α-Galactosidases, β-Glucosidases, β-Mannosidases. In addition the enzymes involved in the hydrolysis of arabinogalactan include β-Galactosidase and Endo-α-L-arabinanase. These enzymes can be found under the following EC numbers such as: EC 3.2.1.8, EC 3.2.1.37, EC 3.2.1.55, EC 3.2.1.99, EC 3.2.1.139, EC 3.2.1.78, EC 3.2.1.25, EC 3.2.1.22, EC 3.2.1.21, EC 3.2.1.89, EC 3.1.1.72, EC 3.1.1.6, EC 3.1.1.73.

"Hemicellulose" refers to a group of complex carbohydrates found in a lignocellulosic material that, with other carbohydrates (e.g., pectins), surround the cellulose fibres of plant cells. The composition of hemicelluloses is dependent on the plant type. Most common types of hemicelluloses include xylan, glucoronoxylan, glucomannan, galactoglucomannan, arabinoxylan, xyloglucan and arabinogalactan.

Nutrients supplemented in a microorganism cultivation medium refer to compounds and components enabling the growth of a microorganism and/or the production of lipids or promoting growth and lipid production. These include typically various sources of carbon, nitrogen and phosphorus, inorganic salts and trace elements. The cultivation medium can be supplemented with natural or man-made fractions, which contain carbohydrates, preferably carbohydrate polymers containing hexose sugar, pentose sugar, either one or both of these, or fractions, which contain cellulose, starch, non-starch polysaccharide, chitin, or lignocellulose. The supplementation of nutrients in the cultivation medium is not absolutely necessary, but may be advisable in certain cases.

The cultivation conditions suitable for the production of lipids refer to conditions in which the formation and/or accumulation of lipids takes place in response to the composition of a cultivation medium, cultivation condition, an external factor or both.

The cultivation conditions suitable for the production of enzymes refer to conditions in which the formation and accumulation of enzymes takes place in response to the composition of a cultivation medium, cultivation condition, an external factor or both.

In an embodiment of the invention the enzyme production is initiated and/or maintained by adding an enzyme inducer into the microorganism culture. Generally this results in increased amount of produced enzymes. In particular in continuous cultivations it is important to maintain the amount of inducers on sufficient level to maintain the production of extracellular enzymes.

The enzymes as described herein can be inducible or constitutive.

Enzyme induction (Inducibility of enzymes) refers to increment in de novo synthesis of enzymes by the presence of an inducing factor.

According to a preferred embodiment of the invention, a microorganism capable of using extracellular polymeric or oligomeric compounds, such as sugars, as their nutrition, such as carbon and/or energy sources, are cultivated on a cultivation medium comprising polymeric biomass containing these compounds. The microorganism is allowed to produce lipids and enzymes.

"A cultivation medium" refers here to a medium used for cultivating microorganisms. The cultivation medium comprises here for example polymeric biomass containing at least partly polymeric or oligomeric compounds, such as polymeric sugars. The cultivation medium may be supplemented with minerals, micronutrients, macronutrients and buffering agents.

A preferred feedstock in some embodiments of the invention is polymeric biomass comprising lignocellulose, cellulose, hemicellulose or lignin, or other components of lignocellulose starch, as such or as a combination, or biomass treated chemically or physically or by their combination in order to improve the access of enzymes to sugar polymers. The polymeric biomass also comprises components that are typically present in single cell organisms.

The pre-treated biomass is for example a biomass comprising hexose and/or pentose sugars or their derivatives. The biomasses may be treated prior to or after enzyme treatment by chemical, physical, thermo-mechanical or biological means or by any combinations thereof and used thereafter for single-cell oil production.

"Polymeric biomass" refers to natural organic material or organic material treated by different chemical or physical methods or by their combination. By polymeric biomass is here meant for example biomass used as feedstock in a biotechnical process, such as in a single-cell oil process. Polymeric biomass may also be an industrial product or a side stream of an industrial process, such as a fraction containing hemicellulose or cellulose, starch, biomass containing starch, non-starch polysaccharide, chitin, polygalacturonic acid, pectin, protein, a microorganism or residue of a microorganism.

In an embodiment of the invention the biomass is a microorganism, such as yeast, bacterium, mould or algae or a component thereof or a side stream of an industrial process comprising these microorganisms.

More specifically, in the present invention it has been found that the single cell oil production process can be directed to production or enhanced production of enzymes, for example hydrolytic enzymes.

In an embodiment of the invention polymeric biomass is treated by enzymes obtained in the process and the products comprise monomeric, dimeric, oligomeric carbohydrates and/or undegraded components inducing or maintaining the enzyme production.

"Lignocellulosic material" or "lignocellulosic biomass" refers to biomass that is composed of cellulose, hemicellulose, and/or lignin or any fractions thereof. Lignocellulosic materials include but is not limited to woody plants or non-woody, herbaceous plants or other materials containing cellulose and/or hemicellulose: Materials can be agricultural residues (such as wheat straw, rice straw, chaff, hulls, corn stover, sugarcane bagasse), dedicated energy crops (such as switchgrass, *Miscanthus*, reed canary grass, willow, water hyacinth), wood materials or residues (including sawmill and pulp and/or paper mill residues or fractions, such as hemicellulose, spent sulphite liquer, waste fibre and/or primary sludge), moss or peat, microorganisms or municipal paper waste. Also low lignin materials, materials such as macroalgae or microalgae biomass can be used. In addition, the materials can be also hemicellulose or cellulose fractions from industrial practises. The invention can utilize any kind of cellulose fraction. The raw materials or certain fractions, such as hemicellulose and/or cellulose, of raw materials from different origin, plant species, or industrial processes can be mixed together and used as raw materials for the bioprocesses according to the invention.

"Saccharification" refers as hydrolysis of polymeric sugars to sugar oligomers and monomers. Saccharification is typically achieved by the use of enzymes capable if hydrolysing polymeric sugars.

"Carbohydrates" stand for organic molecules, incorporating an aldehyde, acid or keto group and, in addition to these, several hydroxyl groups. Thus, the range of hydrocarbons encompasses compounds described by terms such as monosaccharide, oligosaccharide, sugar, cellulose, hemicelluloses, starch and non-starch hydrocarbon.

"Cellulose" is a long-chain polysaccharide, having a primary structure which consists of polymer created by β-1-4 glucose bonds.

"Starch" is a long-chain polysaccharide, consisting principally of α-1-4 and α-1-6 glucose units.

Monosaccharide is a monomeric unit of carbohydrates, $(C—H_2O)_n$, which typically consists of 3-9 carbon atoms and which has stereochemical inconsistencies in one or more carbon atoms. These are represented by hexoses, such as glucose, galactose, mannose, fructose, which have 6 carbon atoms, and pentoses, such as xylose, ribose and arabinose, which have 5 carbon atoms.

Cellulose does not typically dissolve in water in nature. Cellulases include endoglucanases, exoglucanases and β-glucosidases. For example endoglucanases (EC 3.2.1.4), operated mostly on amorfous part of cellulose, attack randomly on internal ponds of cellulose macromolecule. Exoglucanases or cellobiohydrolases (EC 3.2.1.91) attacks on the end of cellulose chain hydrolyzing mainly one cellobiose unit at a time. Exoglucanases are able also to hydrolyse crystalline cellulose polymer. Finally, the hydrolysis of cellobiose to glucose monomers is done by β-glucosidase (EC 3.2.1.21).

Enzymes capable of hydrolysing hemicellulose are for example endoxylanases, endoarabinases and endomannanases. Hemicellulases attacking oligomers after endo-hemicellulases operation are for example β-xylosidase, β-arabinosidase, β-mannosidase and β-glucosidase. The residual side-linkages in oligomers can be broken down by enzymes such as α-glucuronidase, α-arabinodase and α-D-galactosidase. Acetyl-constituents can be removed by esterases.

Further, enzymatic hydrolysis of lignin requires activity of oxidative enzymes such as lignin peroxidase (LiP EC 1.11.1.14), manganese-dependent peroxidase (MnP EC 1.11.1.13) and laccase (EC 1.10.3.2). The chemical structure and attachment of lignin to cellulose and hemicellulose is more important than the amount of lignin.

Side streams or side-stream fractions stand for any aqueous solutions or supernatants releasing from the production of cells, the production of enzymes, the production of single-cell oil, the recovery of cells or the extraction of oil, the recovery of intracellular enzymes, and for a post-lipid extraction mixture of variably broken and intact cells, i.e. a residual cell mass or cell suspension or cell mass.

The single-cell oil production process as described herein can be a continuous, batch or a fed-batch process or any other process assembly aimed at single-cell oil production.

The single cell oil production process can be carried out also in reactors, where the amount of free water is low or where the production is carried out on a solid or semisolid surface. The cell mass or other biomass not dissolving in water, can be extracted with aqueous solutions in order to obtain enzymes into soluble form.

The enzymes can be recovered from microorganism culture, supernatant and microorganism cells by any known and suitable method or by any suitable method developed in the future. The same applies also to methods by which the enzymes can be separated into fractions with the desired enzyme activities.

A method by which the microorganism culture or the supernatant or the enriched protein fraction comprising catalytically active enzyme(s) are recovered by means based on their molecular size, ionic behavior, solubility in water, solubility in different solutes or solubility in mixture solutes containing a buffering factor or a surface active factor or a surface-active compound or a salt.

Microorganism capable of lipid production refers in this description to a microorganism, such as bacterium, archaeum, alga or fungus, typically filamentous fungus or yeast, capable of producing lipid.

"leaginous microorganism" refers here typically to a microorganisms which accumulate at least 15% (w/w) of their biomass as lipid when cultivated in suitable or optimal cultivation conditions.

"A microorganism capable of producing both lipids and enzymes" is typically a fungus, in particular a filamentous fungus (mold) or a yeast, microalga or bacterium. Lipid producing molds, dimorphic molds and filamentous fungi comprise, for example, those in the genera *Absidia, Aspergillus, Blakeslea, Chaetomium, Cladosporium, Claviceps, Clodosporidium, Cunninghamella, Emericella, Entomophthora, Fusarium, Gibberella, Glomus, Humicola, Mucor, Mortierella, Paecilomyces, Penicillium, Puccia, Pythium, Rhizopus, Saprolegnia, Trichoderma, Ustilago* and *Zygorhynchus*, such as molds of the genus *Absidia spinosa, Aspergillus*, for example *A. ficheri, A. flavus, A. nidulans, A. niger, A. ochraceus, A. oryzae, A. sojae* and *A. terreus, Blakeslea trispora, Chaetomium globosum, Cladosporidium herbarum, Claviceps purpurea*, molds of the genus *Cunninghamella*, for example *C. echinulata, C. japonica* and *C. elegans, Entomophthora coronata, Fusarium bulbigenum, Fusarium graminearum, Fusarium* sp., *Gibberella fujikuroi, Glomus calcdonius, Humicola lanuginosa, Humicola grisea*, molds of the genus *Mucor*, for example *M. circinelloides, M. plumbeus* and *M. rouxii*, molds of the genus *Mortierella*, for example *M. isabeffina, M. alpina* and *M. ramanniana*, molds of the genus *Penicillium*, for example *P. javanicum, P. filacinum, P. spinulosum* and *P. soppii, Paecilomyces lilacinus, Puccia coronata, Pythium ultimum, Pythium irregulare, Rhizopus arrhizus, Rhizopus delemar, Rhizopus oryzae, Ustilago zeae, Ustilago maydis, Zygorhynchus moelleri*, as well as *Malbranchea pulchella, Myrothecium* sp., *Sclerotium bataticola, Pellicularia practicola, Sphacelothea reiliana, Tyloposporidium ehren bergii, Achyla americana, Lepista nuda, Tilletia controversa, Cronartium fusiform*.

It is beneficial in the invention to use molds from the phyla Zycomycota or Ascomycota. It is particularly beneficial to use molds from the genera *Aspergillus, Rhizopus, Mucor* or *Mortierella*.

In another embodiment of the invention bacteria from the genera, but not limited to, such as *Streptomyces, Actinomyces, Arthrobacter, Nocardia, Rhodococcus* or *Bacillus* can be used.

Yet in another embodiment of the invention yeasts from the genera, but not limited to *Cryptococcus, Trichosporon, Apiotrichum, Hansenula, Lipomyces, Rhodosporidium, Candida, Yarrowia, Rhodotorula, Sporobolomyces, Sporidiobolus, Trichosporon, Torulopsis, Waltomyces, Endomyces, Galactomyces, Pichia* or *Cryptococcus*, such as *Cryptococcus albidus, C. terricolus, Trichosproron cutaneum, Lipomyces starkeyi, L. lipofera, Rhodosporidium toruloides, Candida curvata, Yarrowia lipolytica, Rhodotorula glutinis, Candida* sp. 107, *Lipomyces* sp. 33, *Rhodotorula gracilis, Trichosporon pullulans* or *T. fermentans* can be used.

Preferred microorganisms belong to fungi, more preferably to genera selected from the group of *Aspergillus, Trichoderma, Rhizopus* and *Humicola*, or from yeast *Cryptococcus*. Most preferably the microorganism belongs to genus *Aspergillus*.

Oleaginous microorganisms that are genetically modified to be able to utilize polymeric sugars in hemicellulose are also part of the invention. Further, organisms capable of utilizing polymeric sugars in cellulose or hemicellulose that are genetically modified to improved production of lipids are also included in this invention.

In one embodiment of the invention the enzyme preparation is introduced into a biotechnical process, which uses a microorganism not capable of producing hydrolytic enzymes. In another embodiment the biomass used in said process is pre-treated with the enzyme preparation, which is preferably the supernatant or the protein fraction comprising catalytically active hydrolytic enzyme(s). The biotechnical process uses typically a microorganism, such as yeast, bacteria, algae, archaea, filamentous fungus (mould) or a component thereof.

After removal of biologically active proteins the fermentation liquor is introduced into another biotechnical process, or re-cycled back to the same process, or it may be released to the environment or led to a waste water treatment process. The fermentation liquor may be used as such or treated microbiologically, chemically and/or physically before use or before release into the environment.

According to a preferred embodiment of the invention the process water, residual biomass, and enzymes are re-circulated within the process in such a way that residual biomass is pre-treated with the recovered enzymes and the resulting biomass and process water is introduced to the same or subsequent single cell oil production process.

As described herein the substantially protein free water produced by the process of the invention is introduced into other processes, or applications or to environment. Before other uses, other components, such as organic matter, inorganic salts or non-protein based components may be removed or reduced in the water.

In an embodiment of the invention polymeric biomass or polymeric sugars is treated with the enzymes recovered as described herein in such a way that the enzymatic degradation product of the biomass comprises fermentable carbohydrates and preferably also oligomeric carbohydrates, which when introduced into a new fermentation process cause and maintain extracellular enzyme production.

The enzyme fractions or enzymes recovered in the invention can be used to hydrolyze lignocellulose to subfractions, such as cellulose, hemicellulose or lignin fractions.

In a preferred embodiment of the invention, lipids, proteins, in particular hydrolytic enzyme, are recovered in the invention.

In one aspect, the present invention provides also an enzyme preparation obtained by the process according various embodiments of the invention. The enzyme preparation comprises typically the protein fraction in the aqueous phase of the microorganism culture or in the supernatant and is enriched at least 1 time (1×), preferably at least 2 times (2×), more preferably at least 3 times (3×) calculated as enzyme activity per volume and/or per dry total protein.

In some embodiments of the invention the enzyme preparation may be enriched from the microorganism culture or from the supernatant at least 5 times, in some embodiments at least 10×, or 20× or 30×, or 40×, or 50×, or 60×, or 70×, or 80×, or 90×, or 100× calculated as the enzyme activity per volume and/or per total protein.

In one aspect, the present invention provides also use of the enzymes or enzyme preparation produced according to various embodiments of the invention in another industrial process or in the same or another single cell oil production process or for treating the polymeric biomass used as feedstock in said processes.

In one aspect, the present invention provides also use of the lipids produced according to various embodiments of the invention or as a component of biofuel or as a starting material for biofuel production.

According to a preferred embodiment of the invention lipids produced as described herein are used as biodiesel or renewable diesel, gasoline or jet fuel.

Biofuel Production from Lipids

"Biofuel" refers to solid, liquid or gaseous fuel mainly derived from biomass or biowaste and is different from fossil fuels, which are derived from the organic remains of prehistoric plants and animals.

According to EU directive 2003/30/EU "biodiesel" refers to a methyl-ester produced from vegetable oil or animal oil, of diesel quality to be used as biofuel. More broadly, biodiesel refers to long-chain alkyl esters, such as methyl, ethyl or propylesters, from vegetable oil or animal oil of diesel quality. Biodiesel can also be produced from microorganism lipids, whereby microorganism lipid can originate from a bacterium, a fungus (a yeast or a mold), an algae or another microorganism.

"Renewable diesel" refers to a fuel which is produced by a hydrogen treatment of lipids of an animal, vegetable or microorganism origin, or their mixtures, whereby microorganism lipid can originate from a bacterium, a fungus (a yeast or a mold), an algae or another microorganism. Renewable diesel can be produced also from waxes derived from biomass by gasification and Fischer-Tropsch synthesis. Optionally, in addition to hydrogen treatment, isomerization or other processing steps can be performed. Renewable diesel process can also be used to produce jet fuel and/or gasoline. The production of renewable diesel has been described in patent publications EP 1396531, EP1398364, EP 1741767 and EP1741768.

Biodiesel or renewable diesel may be blended with fossil fuels. Suitable additives, such as preservatives and antioxidants may be added to the fuel product.

"Lubricant" refers to a substance, such as grease, lipid or oil that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demulsifiers, antifoaming agents, cosolvents, and lubricity additives (see for example U.S. Pat. No. 7,691, 792). Base oil for lubricant can originate from mineral oil, vegetable oil, animal oil or from a bacterium, fungi (a yeast or a mold), an algae or another microorganism. Base oil can also originate from waxes derived from biomass by gasification and Fischer-Tropsch synthesis. Viscosity index is used to characterise base oil. Typically high viscosity index is preferred.

The lipids produced according with the method described in this invention can be used as feedstock for the production of biodiesel, renewable diesel, jet fuel or gasoline. Biodiesel consists of fatty acid methyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogen deoxygenation, hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications.

Lipids produced with the method can be used as base oils for lubricants (lubrication oils) or as a starting material for production of base oils for lubricants.

The term "acyglycerol" refers to an ester of glycerol and fatty acids. Acylglycerols occur naturally as fats and fatty oils. Examples of acylglycerols include triacylglycerols (TAGs, triglycerides), diacylglycerols (diglycerides) and monoacylglycerols (monoglycerides).

Recovery of Oil

Microorganisms containing lipids may be separated from culture medium by any known methods, such as using a filtration or decanting techniques. Alternatively, centrifugation with industrial scale commercial centrifuges of large volume capacity may be used to separate the desired products.

In various embodiments of the invention, oil, or precursors for oil, may be recovered from cell biomass or culture broth using any method known in the art or developed in the future. Such methods, include, but are not limited to extraction with organic solvents. In various embodiments of the invention, microorganism cells may be disrupted to facilitate the separation of oil and other components. Any method known for cell disruption may be used, such as ultrasonication, osmotic shock, mechanical shear force, cold press, thermal shock, enzyme-catalyzed or self-directed autolysis.

The oil extracted cell residue can be used for energy production, e.g. combusted or treated with anaerobic digestion process, or utilized as animal feed. Oilextracted cell residue, or a fraction of the cell residue, can also be recycled back to the bioprocesses to be used as a source of nutrients.

In addition to the recovery of lipids and enzymes it is also within the scope of the invention to recover other economically utilizable components or components from the side streams of single-cell oil process or One embodiment of the invention is presented in FIG. 1.

Polymeric biomass can be pre-treated mechanically, thermomechanically, chemically or by a combination of these methods.

The treated material is introduced to enzyme treatment. The enzymes originate at least partly from the fractions, typically from process water of a single cell oil production process. The enzyme treatment is optionally followed by physical or chemical treatment or combinations thereof. These treatments and enzymatic treatments may be repeated one or more times.

The treated biomass is introduced into a single-cell oil production process allowing the microorganism to produce lipids.

The cells and solid phase are separated from liquid phase (supernatant). Macromolecular components are recovered from the liquid phase by using methods maintaining a substantial amount of the enzymatic activity. The enzymatically active components can be introduced to treat biomass used in single cell oil production process or they may be introduced to the single cell oil production process. Optionally enzyme preparations may be prepared from the enzymatically active components and the thus obtained enzyme preparations sold or used in other processes. The released water is optionally introduced into the single cell oil process or for other use or it may be released out from the system.

The solid substance fraction releasing from the single-cell oil production process is treated to separate and to recover the desired components, in particular lipids, in some embodiments also enzymes.

Illustrative Embodiments

In summary, various embodiments of the invention are described below with the aid of the following numbered clauses 1-22. The embodiments are illustrative and are not intended to limit the claimed subject matter.

Clauses

1. A process for producing enzymes, which comprises
   cultivating a microorganism capable of producing both single cell oil and enzymes under conditions suitable for single cell oil production and enzyme production in a single cell oil production process, and producing single cell oil and enzymes by said microorganisms;
   obtaining a microorganism culture comprising single cell oil and enzymes, and recovering at least part of (i) the microorganism culture, of (ii) the supernatant and/or microorganism cells separated from the microorganism culture, of (iii) protein fraction enriched from the supernatant, and/or of (iv) protein fraction from the cells, for use as an enzyme preparation or as a source of enzymes, and
   recovering single cell oil from the microorganism cells.
2. The process according to clause 1, wherein the enzymes are extracellular and recoverable from the supernatant.
3. The process according to clause 1 or 2, wherein the cultivation medium is solid or semisolid and the enzymes are introduced to aqueous phase before recovery.
4. The process according to any one of clauses 1 to 3, wherein the microorganism culture or part thereof or the supernatant or part thereof is/are re-circulated in the process.
5. The process according to any one of clauses 1 to 4, wherein the process water released from the process comprises at least 5%, preferably at least 10% less proteins than the process water of a single cell oil process without enzyme recovery.
6. The process according to any one of clauses 1 to 5, wherein the process water released from the process comprises at least 5%, preferably at least 10% lower biological oxygen demand compared to the biological oxygen demand of a process water of a single cell oil process without enzyme recovery.
7. The process according to any one of clauses 1 to 6, wherein the aqueous phase of the microorganism culture or the supernatant is concentrated.
8. The process according to clause 1, wherein the enzymes are intracellular and obtainable from the microorganism cells.
9. The process according to clause 8, wherein the cell residues after enzyme recovery comprise at least 1%, preferably at least 10% less proteins than the cell residues of a single cell oil process without enzyme recovery from the cells.
10. The process according to any one of the clauses 1-9, wherein the enzyme production is initiated and/or maintained by adding an enzyme inducer into the microorganism culture or the enzyme production occurs constitutively.
11. The process according to any one of the clauses 1-10, wherein the enzyme production and single cell oil production occur simultaneously or sequentially in any order.
12. The process according to any one of clauses 1-11, wherein the microorganism is cultivated on a medium comprising polymeric biomass, such as lignocellulose or fractions thereof as carbon source.

13. The process according to any one of clauses 1-12, wherein the enzymes comprise hydrolases, oxidoreductases, lyases, isomerases, transferases or ligases or any mixtures thereof.
14. The process according to any one of clauses 1-13, wherein the enzyme hydrolyses glycosidic bonds.
15. The process according to any one of clauses 1-14, wherein the microorganism is a fungus or a yeast, the fungus preferably belonging to a genus selected from the group of *Aspergillus, Trichoderma, Rhizopus* and *Humicola*, or the yeast belonging to *Cryptococcus*, the fungus being more preferably of genus *Aspergillus*.
16. An enzyme preparation obtained by the process according to any one of clauses 1 to 15.
17. The enzyme preparation according to clause 16, wherein the protein fraction in the aqueous phase of the microorganism culture or in the supernatant is enriched and optionally purified, stabilized, dried and/or formulated.
18. Use of the enzymes produced according to the process of any one of clauses 1-15 or enzyme preparation according to clause 16 or 17 in the same or another industrial process.
19. Use of the lipids produced according to the process of any one of clauses 1-15 or the enzyme preparation according to clause 16 or 17 as a biofuel, component of biofuel or as a starting material for biofuel production.
20. The use according to clause 19, wherein the biofuel is biodiesel or renewable diesel, gasoline and/or jet fuel.

It is an object of the following examples to illustrate the invention and shall not be construed as limiting the invention in any way.

EXAMPLES

The enzyme activities in spent culture broth from cultivations of fat-producing filamentous fungi were determined by hydrolysis tests with pure cellulose and xylan as substrates.
Methods
Sugar Definition:
In order to define the sugar concentration of a solution, the solution was made into. a suitable dilution which was filtered through 0.2 μm prior to an HPLC analysis.

The column used in sugar definition was Shodex Sugar SP 0810 ion-exchanger in lead form (in stationary phase). The column dimensions were 8.0 mm (ID)×300 mm. The eluent was water (flow rate 0.6 ml/min) and the column temperature was 60° C. The detector was RI Shimatzu RID 10A and the pump was A6 and the autosampler was Shimatzu SIL 20A. The processing of results was conducted with Class-VP software.
Fatty Acid Analysis:
The fatty acid composition of samples was determined as in the method described by Suutari et al. (1990). Lipids in the samples were first hydrolyzed into free fatty acids, which were saponified into sodium salts thereof and thereafter methylated into methyl esters. The fatty acid methyl esters were analyzed gas chromatographically.
Protein Concentration Analysis:
The protein concentration of the culture broths were analysed after filtration of the broth through Whatman3 filterpaper. The protein concentration was analysed according to the Bio-Rad Protein Assay (based on Bradford method).
Hydrolysis Tests:
The spent culture broth was filtered through Whatman3 filterpaper before the hydrolysis test.

The xylanase activity was determined as follows. A 100 ml Erlenmeyer flask was used as the reaction vessel. It was filled with 20 ml 1% birch wood xylan (Sigma) solution in phosphate buffer (0.02 M, pH 5) as substrate, 10 ml filtered culture broth and 20 ml phosphate buffer (0.02 M, pH 5). The hydrolysis reaction was performed in an agitated (140 rpm) water bath at 50° C. Samples of 1 ml were taken from the reaction vessel directly after the addition of the culture broth and after 1, 3, 5, 21/23 hours. The hydrolysis reaction was stopped in the 1 ml sample by decreasing the pH by the addition of 50 μl of 1.33 M sulphuric acid. Samples were treated for salt and polymeric sugar removal to suit HPLC-analysis. The released sugars were analysed by HPLC (see Sugar definition) with mannitol as standard.

Cellulase activity was determined with 1 g Whatman filter paper as cellulose substrate instead of xylan. The reaction volume was 50 ml containing 1 g Whatman filter paper in equal sized circles (ca. 5 mm diameter) as substrate, 10 ml filtered culture broth and 40 ml phosphate buffer (0.02 M, pH 5). The experiment was otherwise performed as with xylan.
Microorganism Strains:
Lipid producing microorganisms are generally available to the public from a plurality of recognized microbial culture (strain) collections, such as ATCC, DSM, etc. Various embodiments of the invention are discussed in the following examples by using microorganism strains as follows. *Aspergillus oryzae* DSM 1861, *Aspergillus oryzae* DSM 1864 and *Aspergillus terreus* DSM 1958.

Example 1

This example shows the enzymatic activity formed in the culture broth during the cultivation of *Aspergillus oryzae* with hemicellulose based material as carbon source for the production of lipids.

*Aspergillus oryzae* was grown in flask cultures with purified birch xylan (Sigma) and spruce and birch hemicelluloses extracted with pressurized hot water extraction as carbon source. Cultivations were done in 250 ml Erlenmeyer flasks containing 50 ml culture medium. The growth medium base contained per liter of water 1 g $(NH_4)_2SO_4$, 1 g $MgSO_4.7H_2O$, 0.5 g $K_2HPO_4$, 1 g $KH_2PO_4$ and 0.2 g $CaCl_2.2H_2O$ and was supplemented with carbon source, yeast extract and optionally support material. Cultivation media were inoculated with 1% (v/v) fungal spore suspension and the cultures were incubated at 28° C. temperature.

In the case of purified xylan the medium base was supplemented with per liter 40 g purified birch xylan (Sigma) and 1 g yeast extract. Duplicate cultivations were incubated in orbital shaker (160 rpm) for 6 days.

In the case of spruce and birch hemicellulose the medium base was supplemented with per liter 44 g of dried spruce or birch hemicellulose produced by hot water extraction, 0.5 g yeast extract and 2 g cellulose to give mechanical support for the fungal mycelium. Triplicate cultivations were incubated in orbital shaker (180 rpm) for 7 days.

After incubation the culture broth was filtered through Whatman 3 filter paper. Protein concentration and enzyme activities were determined from the filtrate. The retentate was washed with distilled water and dried. Biomass concentration and lipid content were determined from the dried samples.

On purified birch xylan after 6 d cultivation *A. oryzae* fungus produced 16 g/l biomass (dry weight) and the biomass contained 10.5% lipids/dry weight. *Aspergillus oryzae* grown on water extracted birch hemicellulose produced 14 g/l dry biomass during 7 d incubation. The biomass containing fungal mycelium, residual hemicellulose and cellulose contained 8.9% lipids/dry weight equalling to 1.26 lipids per liter of cultivation medium. For lipid production both birch xylan and hemicellulose were better than spruce hemicellulose as on spruce hemicellulose 8.7 g/l dry biomass containing 3.7% lipids/dry weight was produced.

The protein concentration of the culture broths were 0.06 and 0.02 mg/ml for the spruce and birch hemicellulose cultivations and 0.05 mg/ml for the birch xylan cultivation.

Figure 2:
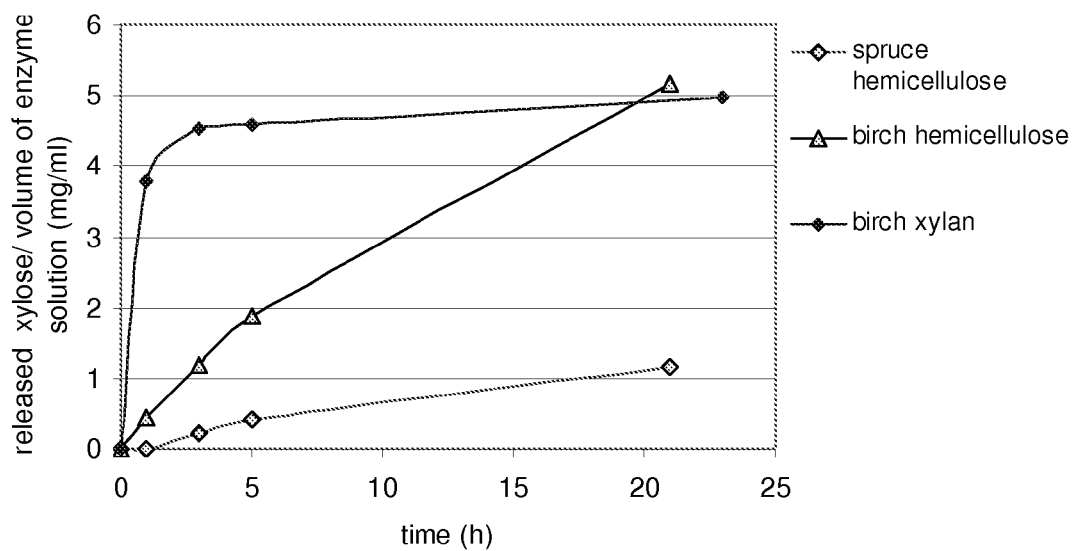
FIG. 2 Xylose released in the hydrolysis test per volume of culture broth. As substrate was used 200 mg birch wood xylan.
Figure 3:
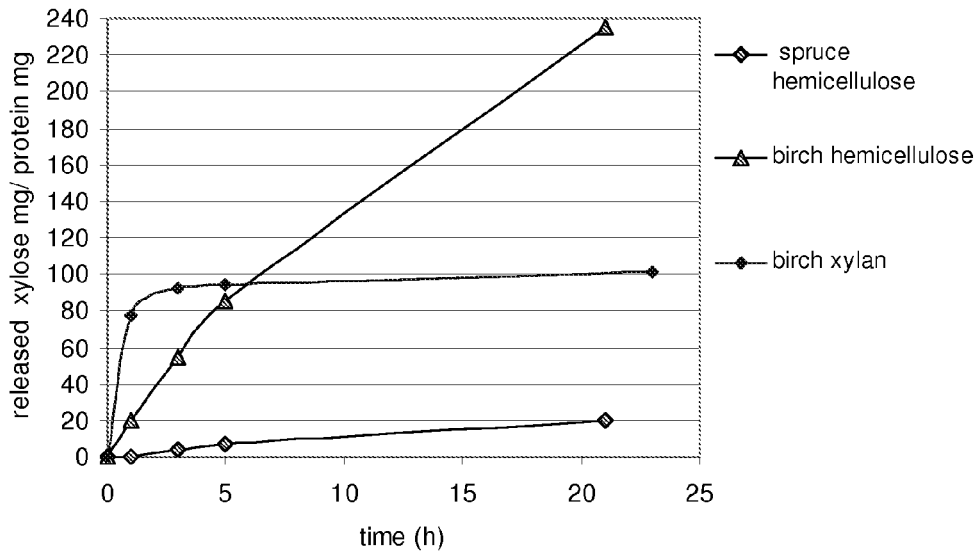
FIG. 3 Xylose released in the hydrolysis test per protein. As substrate was used 200 mg birch wood xylan.

The released xylose from the xylan hydrolysis test as a function of time per milliliter culture broth and per milligram of protein in the reaction is presented in FIGS. 2 and 3. FIG. 2 shows the xylose released in the hydrolysis test per volume of culture broth. As substrate was used 200 mg birch wood xylan. FIG. 3 shows the xylose released in the hydrolysis test per protein. As substrate was used 200 mg birch wood xylan.

One milliliter of culture broth from the spruce hemicellulose cultivation released 1.2 mg of xylose in 21 h and 20.1 mg/mg protein. One milliliter of culture broth from the birch hemicellulose cultivation released 5.2 mg of xylose in 21 h and 234.6 mg/mg protein. One milliliter of culture broth from the birch xylan cultivation released 5.0 mg of xylose in 23 h and 101.4 mg/mg protein.

The culture broths from *Aspergillus oryzae* cultivations with hemicellulose or xylan carbon source showed significant xylanase activity. The culture broths had no detectable cellulase activity as no free glucose was detected in the cellulose hydrolysis test.

Example 2

This example shows the enzymatic activity formed in the culture broth during the cultivation of *Aspergillus oryzae* with cellulose based material as carbon source for the production of lipids.

*Aspergillus oryzae* was cultured for lipid production on different cellulose based lignocellulose materials. The growth medium base contained per liter of water 40 g lignocellulosic material as carbon source, 0.5 g yeast extract, 1 g $MgSO_4 \cdot 7H_2O$, 0.5 g $K_2HPO_4$, 1 g $KH_2PO_4$ and 0.2 g $CaCl_2 \cdot 2H_2O$ and was supplemented with nitrogen source and trace metals.

Experiments 1-4 were performed as flask cultures. In experiments 1-3 the medium base was supplemented with 3 g $NaNO_3$ and 0.02 g $FeSO_4 \cdot 7H_2O$ per liter and in experiment 4 the medium base was supplemented with 1 g $(NH_4)_2SO_4$ per liter. Parallel cultivations were done in 250 ml Erlenmeyer flasks containing 50-100 ml culture medium. Cultivation media were inoculated with 1% (v/v) *Aspergillus oryzae* spore suspension. The cultures were incubated at 28° C. temperature in orbital shaker (160 rpm) for 6 days.

Experiments 5-6 were performed as bioreactor fermentations.

In experiment 5 the growth medium base was supplemented with 1.46 g peptone, 0.00015 g $ZnSO_4 \cdot 7H_2O$, 0.0001 g $CuCl_2 \cdot 2H_2O$ and 0.00625 g $MnCl_2 \cdot 4H_2O$ per liter. The carbon source was cellulose which was added to the cultivation to give a final concentration of 50 g/l. The cultivation medium was inoculated with 50 ml 48 h precultured *Aspergillus oryzae* suspension. The fermentation was performed in 1 L culture medium volume at 28° C. temperature with 0.8 l/min aeration and 350-450 rpm agitation. Culture pH was 5.7 and it was adjusted with 3 M NaOH during the cultivation. Enzyme activities were determined after 188 h incubation.

In experiment 6 the culture medium base was supplemented with 6.5 g peptone, 0.00015 g $ZnSO_4 \cdot 7H_2O$, 0.0001 g $CuCl_2 \cdot 2H_2O$ and 0.00625 g $MnCl_2 \cdot 4H_2O$ per liter growth medium base. The carbon source was cellulose which was added to the cultivation to give a final concentration of 55 g/l. For inoculation spore suspension was prepared by applying in total 24 ml of sterile water on two sporulating *A. oryzae* PDA petri plate cultures. The spores were suspended with a spreader and 1 L culture medium was inoculated with the suspension. The fermentation was performed at 28° C. temperature with 0.6 l/min aeration and 350-450 rpm agitation. Culture pH was 5.7 and it was adjusted with 3 M NaOH during the cultivation. Enzyme activities were determined after 233 h incubation.

The cultures broths were separated and the protein concentration and the xylanase and cellulase activity assayed as described above.

TABLE 1

The nitrogen and carbon source, culture volume, as well as determined protein concentration and determined enzyme activities.

| Exp | Carbon source | Nitrogen source | Culture volume (ml) | Protein conc. (mg/ml) | Cellulase activity | Xylanase activity |
|---|---|---|---|---|---|---|
| 1 | Hand tissues[1], ground with a Fritsch pulverisette-grinder | $NaNO_3$ | 50 | 0.19 | No | Yes |
| 2 | SolkaFloc (purified cellulose) | $NaNO_3$ | 100 | 0.11 | Yes | Yes |
| 3 | Cellulose[2], milled and sieved, 0.2 mm | $NaNO_3$ | 100 | 0.06 | Yes | Yes |
| 4 | Birch flour (ground with a turborotor) | $(NH_4)_2SO_4$ | 100 | 0.18 | Yes | Yes |
| 5 | Cellulose[2], same treatment as in exp. 3 | Peptone | 1000 | 0.49[3] | No | Yes |
| 6 | Cellulose[2], same treatment as in exp. 3 | Peptone/ $(NH_4)_2SO_4$ | 1000 | 0.11 | No | Yes |

[1]Fiber raw material: recycled fibre
[2]Birch sulphate pulp, bleached, hemicellulose ca. 10%.
[3]Broth concentrated three fold by ultrafiltration (10 000 Da filter in an Amicon Ultra 8200 stirred ultrafiltration cell from Millipore)
In experiment 6 the lipid content was measured to be 4%

Figure 4:
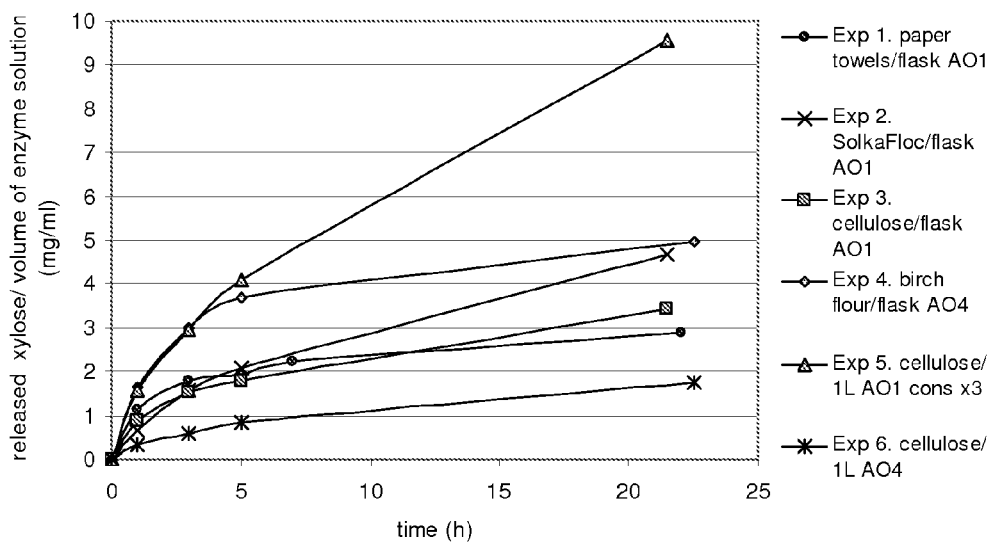
FIG. 4 Xylose released in the hydrolysis test per volume of culture broth. As substrate was used 200 mg birch wood xylan.
Figure 5:
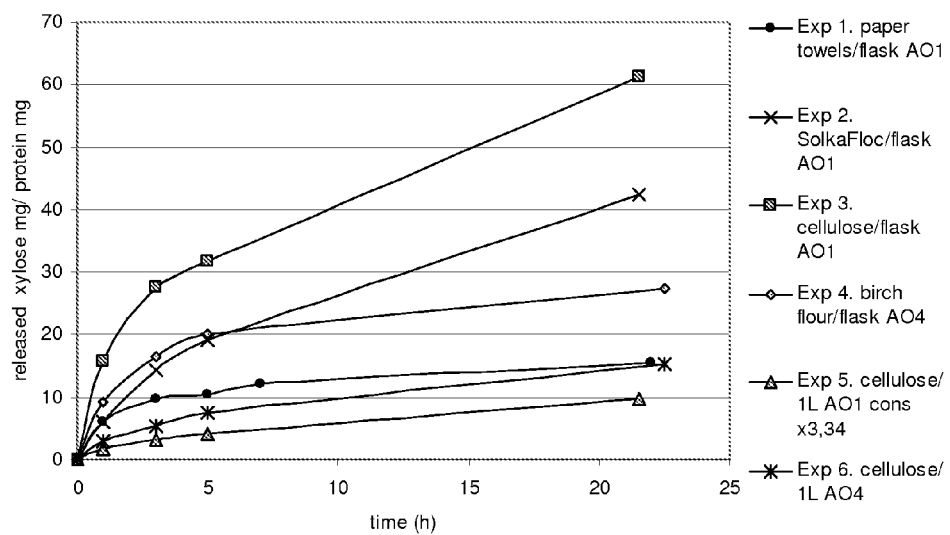
FIG. 5 Xylose released in the hydrolysis test per protein. As substrate was used 200 mg birch wood xylan.

The sugar released during the hydrolysis tests as milligram per milliliter culture broth and milligram per milligram protein as a function of time is presented in 4-7. FIG. 4 shows the xylose released in the hydrolysis test per volume of culture broth. As substrate was used 200 mg birch wood xylan. FIG. 5 shows the xylose released in the hydrolysis test per protein.

Figure 6:
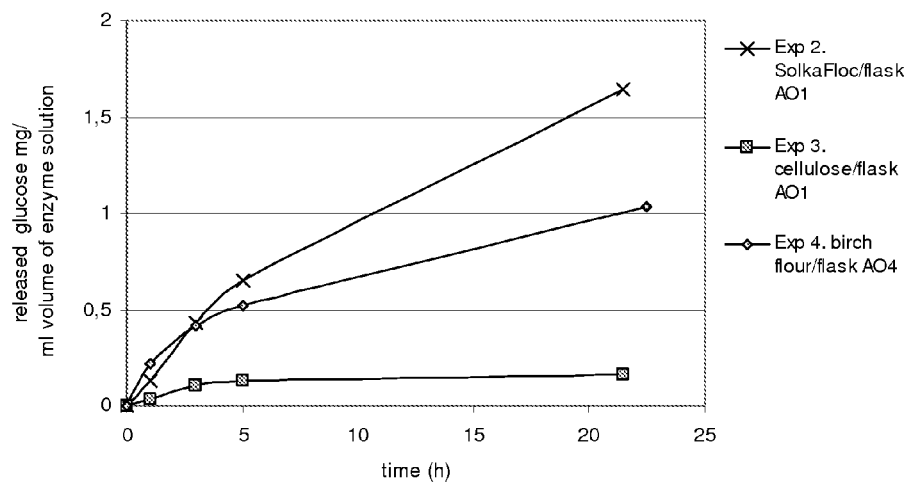
FIG. 6 Glucose released in hydrolysis tests per volume of culture broth. As substrate was used 1 g cellulose.
Figure 7:
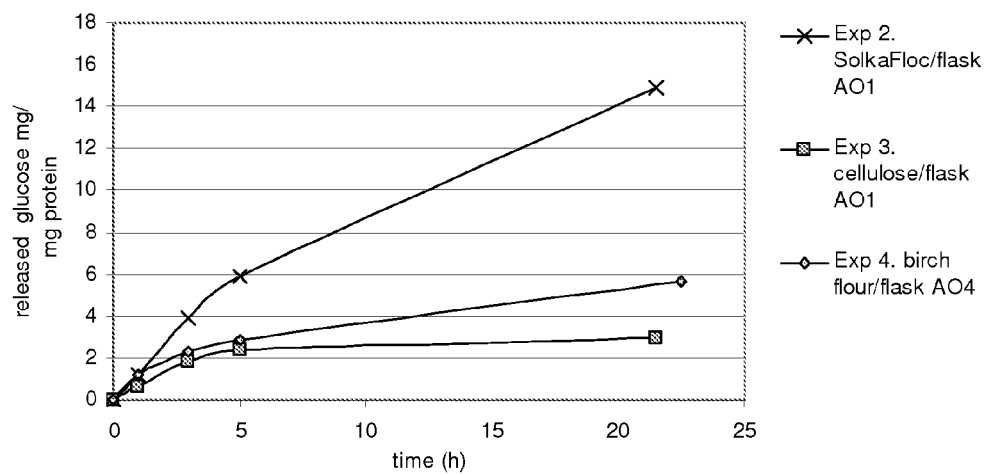
FIG. 7 Glucose released in the hydrolysis test per protein. As substrate was used 1 g cellulose.

As substrate used 200 mg birch wood xylan. FIG. 6 shows the glucose released in hydrolysis tests per volume of culture broth. As substrate 1 g cellulose was used. FIG. 7 shows the glucose released in the hydrolysis test per protein. As substrate 1 g cellulose was used.

All six tested culture broths from cultivations showed significant xylanase activity. Only three of the six culture broths showed signs of cellulase activity indicating a weak ability to produce these enzymes in specific conditions.

This example shows that *Aspergillus oryzae* can produce lignocellulolytic enzymes to the culture broth. The example shows that *A. oryzae* has both xylan and cellulose degradation activity.

Example 3

This example shows the enzymatic activity formed in the culture broth during the cultivation of *Aspergillus terreus* with hemicellulose based material as carbon source for the production of lipids.

*Aspergillus terreus* was cultivated for lipid production on a wheat straw hemicellulose as carbon substrate in 2 liter volume in a bioreactor. The culture medium comprised of 50 ml Yeast Nitrogen Base w/o Amino Acids and Ammonium sulphate (Difco) 10× stock solution suspended in 2 L water and supplemented with per liter: 1.0 g yeast extract, 1 g $(NH_4)_2SO_4$, 1 g $MgSO_4.7H_2O$, 0.5 g $K_2HPO_4$, 1 g $KH_2PO_4$, 0.2 g $CaCl_2.2H_2O$ and 2 g cellulose. The culture medium was inoculated with 150 ml 24 h precultured *A. terreus* culture. The fermentation was performed at 35° C. temperature with 3.0 l/min aeration and 200-430 rpm agitation. Culture pH was 5.7 and it was adjusted with 3 M NaOH during the cultivation. During the cultivation hemicellulose solution was fed to the fermentor. Enzyme activities were determined after 165 h incubation.

The culture broth was separated and it was partly concentrated by ultrafiltration in an Amicon stirred ultrafiltration cell with a 10 000 Da filter (Millipore). The protein and lipid concentration and the xylanase and cellulase activity were assayed as described as above.

The lipid content in the biomass containing fungal mycelium, residual hemicellulose and cellulose was 15% per dry weight. The protein concentration was 0.72 mg/ml in the unconcentrated culture broth and 2.15 mg/ml in the concentrated broth.

The sugar released during the hydrolysis tests as milligram per milliliter culture broth and milligram per milligram protein as a function of time is presented in FIGS. 8 to 11.

Figure 8:
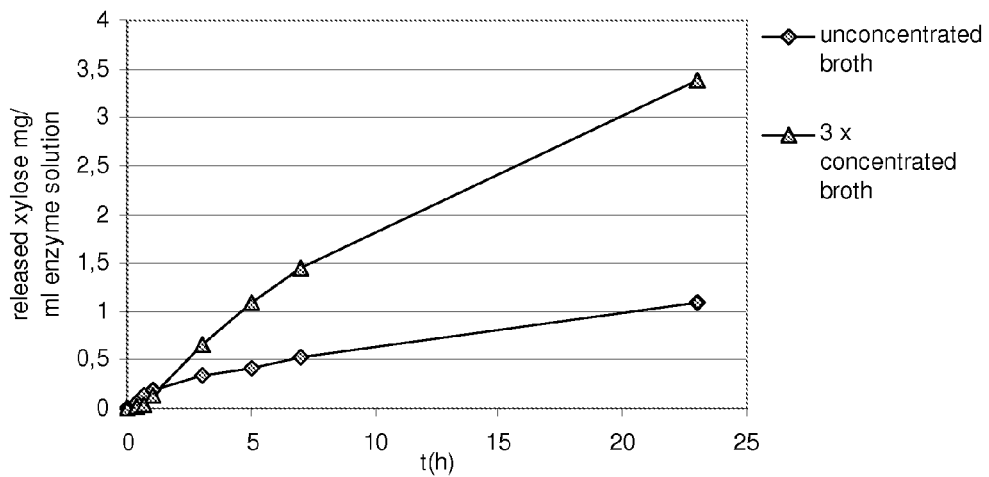
FIG. 8 Xylose released in the hydrolysis test per volume of culture broth. As substrate was used 200 mg birch wood xylan.
Figure 9:
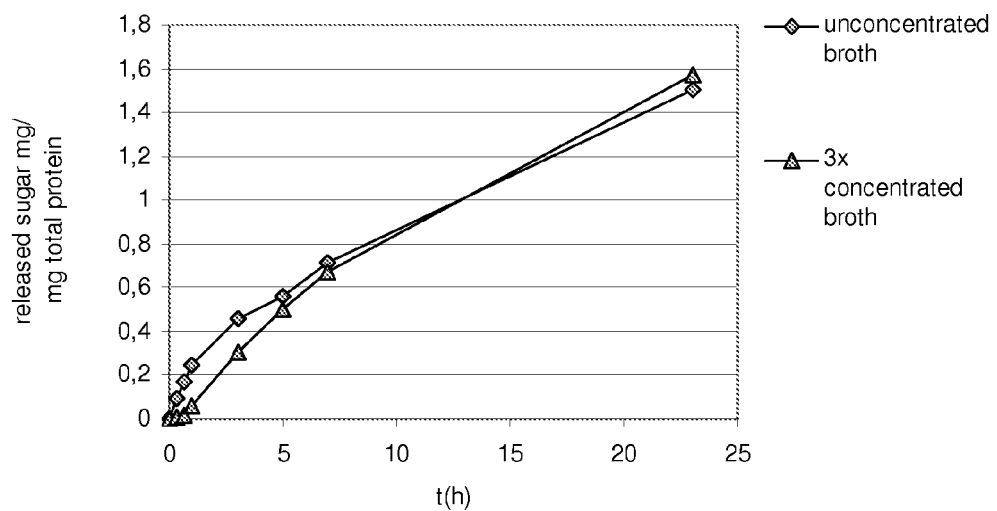
FIG. 9 Xylose released in the hydrolysis test per protein. As substrate was used 200 mg birch wood xylan.
Figure 10:
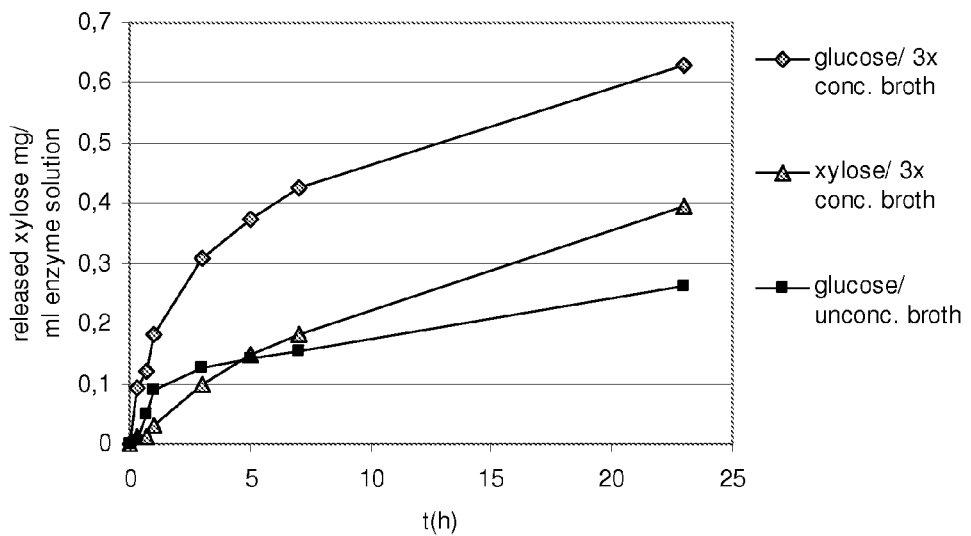
FIG. 10 Glucose released in hydrolysis tests per volume of culture broth. As substrate was used 1 g cellulose. Some xylose was released from the hemicellulose originating from the culture broth used.
Figure 11:
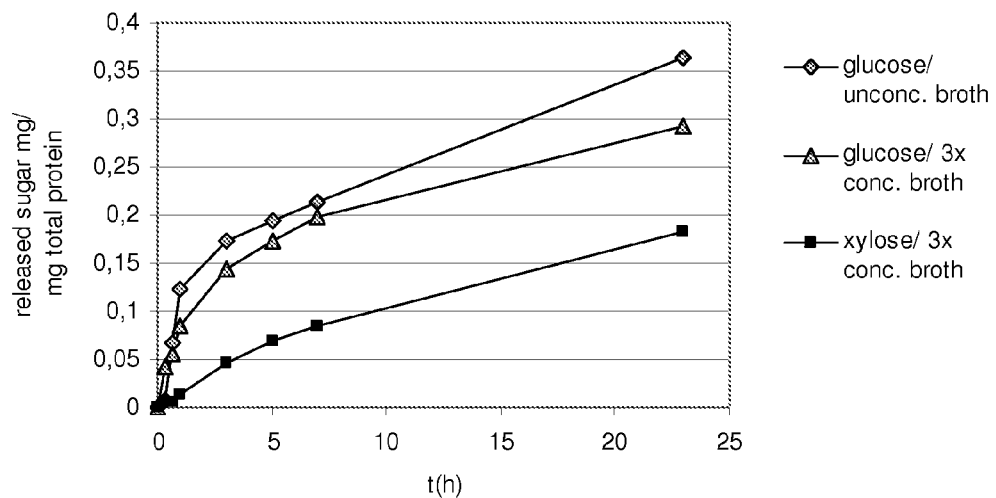
FIG. 11 Glucose released in the hydrolysis test per protein. As substrate was used 1 g cellulose. Some xylose was released from the hemicellulose originating from the culture broth used.

FIG. 8 shows the xylose released in the hydrolysis test per volume of culture broth. As substrate was used 200 mg birch wood xylan. FIG. 9 shows the xylose released in the hydrolysis test per protein. As substrate was used 200 mg birch wood xylan. FIG. 10 shows the glucose released in hydrolysis tests per volume of culture broth. As substrate was used 1 g cellulose. Some xylose was released from the hemicellulose originating from the culture broth used. FIG. 11 shows the glucose released in the hydrolysis test per protein. As substrate was used 1 g cellulose. Some xylose was released from the hemicellulose originating from the culture broth used.

This example indicates that *Aspergillus terreus* can produce both intracellular lipids and extracellular hydrolytic enzymes to the culture broth. The example shows that *A. terreus* produces and excretes to growth medium enzymes that have both xylan and cellulose degradation activity. These enzymes can be separated, concentrated and used in hydrolysis of lignocellulosic material.

Example 4

This example shows the enzymatic activity formed in the culture broth during the cultivation of *Aspergillus oryzae* with hemicellulose based material as carbon source for the production of lipids.

*Aspergillus oryzae* was cultivated for lipid production on a wheat straw hemicellulose as carbon substrate in 2 liter volume in a bioreactor. The culture medium comprised of 50 ml Yeast Nitrogen Base w/o Amino Acids and Ammonium sulphate (Difco) 10× stock solution suspended in 2 L water and supplemented with per liter: 1.0 g yeast extract, 1 g $(NH_4)_2SO_4$, 1 g $MgSO_4.7H_2O$, 0.5 g $K_2HPO_4$, 1 g $KH_2PO_4$ and 0.2 g $CaCl_2.2H_2O$.

The culture medium was inoculated with 200 ml 72 h precultured *A. oryzae* culture. The fermentation was performed in 2 L cultivation medium volume at 30° C. temperature with 3.0 l/min aeration and 200-410 rpm agitation. Culture pH was 5.7 and it was adjusted with 3 M NaOH during the cultivation. During the cultivation hemicellulose solution was fed to the fermentor. Enzyme activities were determined after 144 h incubation.

The culture broth was separated and the protein concentration and the xylanase and cellulase activity assayed as described above. The lipid content in the biomass was containing fungal mycelium and residual hemicellulose 21% per dry weight. The protein concentration was 0.61 mg/ml in the unconcentrated culture broth and 1.65 mg/ml in the concentrated broth.

Figure 12:
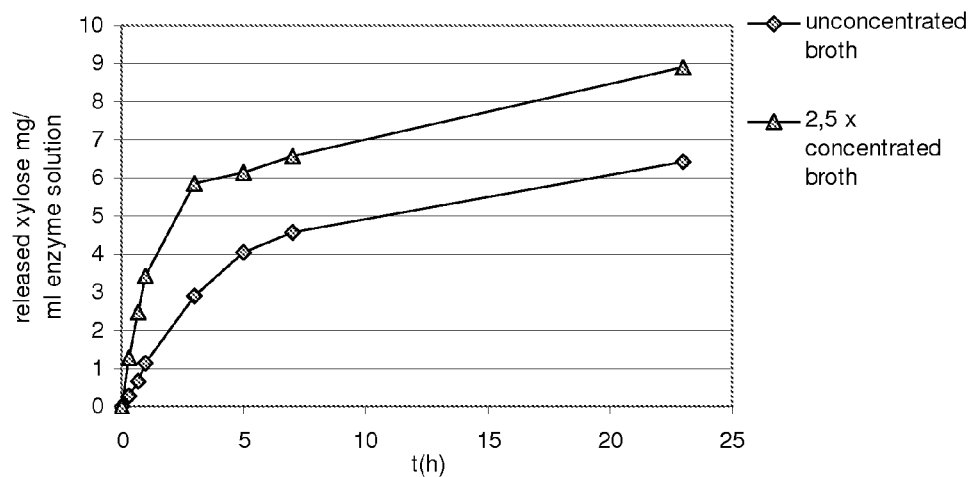
FIG. 12 Xylose released in the hydrolysis test per volume of culture broth. As substrate was used 200 mg birch wood xylan.
Figure 13:
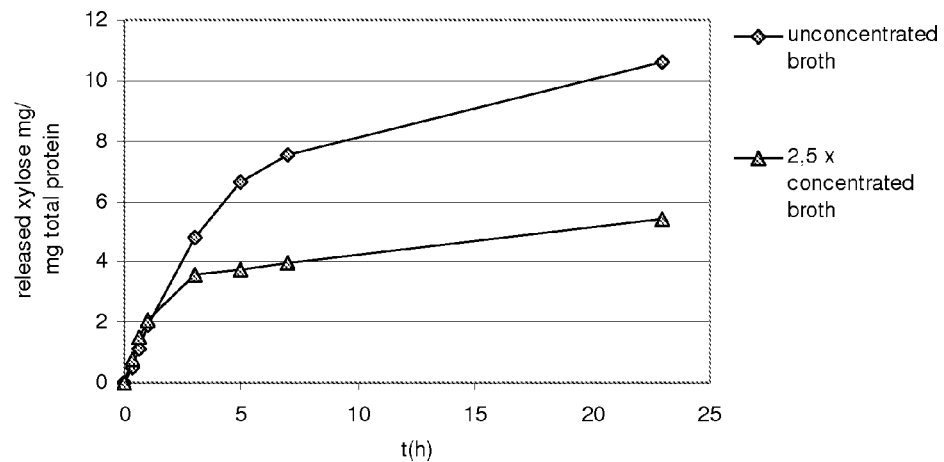
FIG. 13 Xylose released in the hydrolysis test per protein. As substrate was used 200 mg birch wood xylan.
Figure 14:
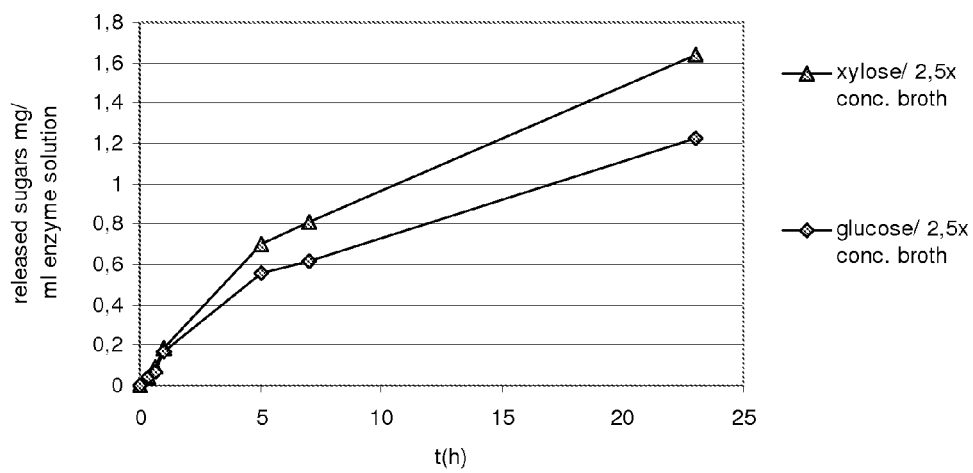
FIG. 14 Glucose released in hydrolysis tests per volume of culture broth. As substrate was used 1 g cellulose. Some xylose was released from the hemicellulose originating from the culture broth used.
Figure 15:
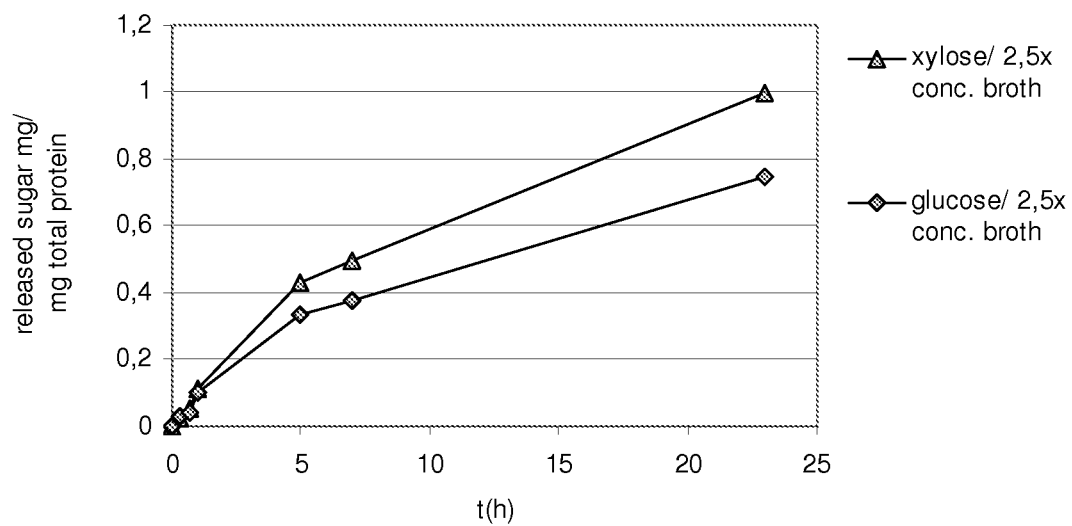
FIG. 15 Glucose released in the hydrolysis test per protein. As substrate was used 1 g cellulose. Some xylose was released from the hemicellulose originating from the culture broth used.

The sugar released during the hydrolysis tests as milligram per milliliter culture broth and milligram per milligram protein as a function of time is presented in FIGS. 12 to 15. FIG. 12 shows the xylose released in the hydrolysis test per volume of culture broth. As substrate was used 200 mg birch wood xylan. FIG. 13 shows the xylose released in the hydrolysis test per protein. As substrate was used 200 mg birch wood xylan. FIG. 14 shows the glucose released in hydrolysis tests per volume of culture broth. As substrate was used 1 g cellulose. Some xylose was released from the hemicellulose originating from the culture broth used. FIG. 15 shows the glucose released in the hydrolysis test per protein. As substrate was used 1 g cellulose. Some xylose was released from the hemicellulose originating from the culture broth used.

This example shows that *Aspergillus oryzae* can produce lipid and as a side product a culture broth with hydrolytic activities that can be used in the hydrolysis of lignocellulose material.

REFERENCES

Suutari M, Liukkonen K, Laakso S. 1990. Temperature adaptation in yeasts: the role of fatty acids. Journal of General Microbiology 136: 1469-1474.

The invention claimed is:

1. A process for producing enzymes, the process comprising:
   (a) cultivating a microorganism capable of producing both single cell oil and extracellular enzymes under conditions suitable for single cell oil production and extracellular enzyme production in a single cell oil production process, and producing single cell oil and enzymes by said microorganism;
   (b) obtaining a microorganism culture comprising single cell oil and extracellular enzymes, and recovering at least part of a protein fraction enriched from supernatant of the culture for use as an enzyme preparation or as a source of enzymes, and (c) recovering single cell oil from the microorganism cells.

2. The process according to claim 1, wherein the microorganism culture or part thereof or the supernatant or part thereof is/are re-circulated in the process.

3. The process according to claim 1, wherein the process produces water and the process water released from the process comprises at least 5%, less proteins than the process water of a single cell oil process without enzyme recovery.

4. The process according to claim 1, wherein the culture comprises an aqueous phase and the aqueous phase of the microorganism culture or the supernatant is concentrated.

5. The process according to claim 1. wherein the enzyme production is initiated and/or maintained by adding an enzyme inducer into the microorganism culture or the enzyme production occurs constitutively.

6. The process according to claim 1, wherein the microorganism is cultivated on a medium comprising polymeric biomass as carbon source.

7. The process according to claim 1, wherein the enzymes comprise hydrolases, oxidoreductases, lyases, isomerases, transferases or ligases or any mixtures thereof.

8. The process according to claim 1, wherein the enzyme hydrolyses glycosidic bonds.

9. The process according to claim 1, wherein the microorganism is a fungus or a yeast.

10. The process according to claim 1, wherein the process produces water and the process water released from the process comprises at least 10% less proteins than the process water of a single cell oil process without enzyme recovery.

11. The process according to claim 6, wherein the biomass comprises lignocellulose or fractions thereof.

12. The process according to claim 9, wherein the fungus belongs to a genus selected from the group consisting of *Aspergillus, Trichoderma, Rhizopus* and *Humicola*.

13. The process according to claim 9, wherein the yeast belongs to genus *Cryptacoccus*.

14. The process according to claim 1, further comprising transesterifying the single cell oil to produce biodiesel.

* * * * *